(12) United States Patent
Beams et al.

(10) Patent No.: US 6,620,848 B2
(45) Date of Patent: *Sep. 16, 2003

(54) NITRIC OXIDE SYNTHASE INHIBITORS

(75) Inventors: Richard Mansfield Beams, Shirley (GB); Martin James Drysdale, Cambridge (GB); Karl Witold Franzmann, London (GB); Anthony Joseph Frend, Stevenage (GB); Harold Francis Hodson, Beckenham (GB); Richard Graham Knowles, Stevenage (GB); Daryl David Rees, Keston (GB); David Alan Sawyer, Beckenham (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 59 days.

This patent is subject to a terminal disclaimer.

(21) Appl. No.: 09/930,605

(22) Filed: Aug. 15, 2001

(65) Prior Publication Data

US 2002/0010366 A1 Jan. 24, 2002

Related U.S. Application Data

(63) Continuation of application No. 09/341,220, filed as application No. PCT/EP98/00096 on Jan. 9, 1998, now Pat. No. 6,369,272.
(60) Provisional application No. 60/069,882, filed on Jan. 13, 1997.

(51) Int. Cl.$^7$ .................. A61K 31/195; C07C 271/06
(52) U.S. Cl. ................ 514/562; 560/148; 562/556
(58) Field of Search .................. 560/148; 562/556; 514/562

(56) References Cited

U.S. PATENT DOCUMENTS

| | | | |
|---|---|---|---|
| 2,049,582 A | | 8/1936 | Ziegler |
| 4,085,217 A | | 4/1978 | Kalopissis |
| 4,512,979 A | * | 4/1985 | Patchett et al. ............. 514/2 |
| 4,594,341 A | * | 6/1986 | Cheung et al. ............ 514/211 |
| 5,028,627 A | | 7/1991 | Kilbourn et al. |
| 5,081,148 A | | 1/1992 | Braquet et al. |
| 5,364,881 A | | 11/1994 | Griffith et al. |
| 5,453,441 A | | 9/1995 | Griffith |
| 5,585,402 A | | 12/1996 | Moncada et al. |
| 5,863,931 A | | 1/1999 | Beams et al. |
| 5,883,251 A | * | 3/1999 | Hansen, Jr. et al. ........ 540/596 |
| 5,889,056 A | | 3/1999 | Hodson et al. |
| 6,369,272 B1 | * | 4/2002 | Beams et al. ............. 562/556 |

FOREIGN PATENT DOCUMENTS

| | | |
|---|---|---|
| DE | 830 640 | 1/1952 |
| DE | 43 10 202 | 10/1993 |
| EP | 0 068173 A | 1/1983 |
| EP | 0 097 031 | 12/1983 |
| EP | 0 200 051 | 12/1986 |
| EP | 0 446 699 | 9/1991 |
| FR | 2727 111 A | 5/1996 |
| GB | 2 240 041 | 7/1991 |
| WO | WO01/04024 | 4/1991 |
| WO | WO93 13055 A | 7/1993 |
| WO | WO95/34534 | 12/1995 |
| WO | WO 96/02245 * | 2/1996 |
| WO | WO 96/21641 * | 7/1996 |

OTHER PUBLICATIONS

Foppoli, C. et al "Oxidative deamination of S–(2–9minoethyl)–homocysteine" Ital. J. Biochem. vol. 29, No. 1, pp. 82–83, 1980.*
Rinali, A., et al., "On the Synthesis of S–beta–aminomethyl–homocysteine", ITALIAN JOURNAL OF BIOCHEMISTRY, vol. 20, No. 1–2, pp. 1–5, Rome, Italy, 1971.
Hope, D.B., et al., "Synthesis of Some Dibasic Sulphurcontaining Amino–acids Related to L–lysine", JOURNAL OF THE CHEMICAL SOCIETY, Section C: ORGANIC CHEMISTRY, No. 12, pp. 1098–1101, Letchworth, GB, 1966.
D. Elmore et al., Biochem. J., 102:728 (1967).
P. Hermann et al., Journal fur praktische Chemie 311:1018 (1969).
Houben–Weyl, Methoden der Organischen Chemie, Georg Thieme Verlag, New York (1985)pp. 931.
U. Larsson et al., Acta Chem Scand 48(6):517 (1994).
B. Plapp et al., Analytical Biochemistry 62:291 (1974).
A. Proudfoot et al., J. Biol. Chem. 264(15):8764 (1989).
D. Rees et al., Br J. Pharmacol. 101:746 (1990).
H. Tanaka et al., J. Biol. Chem. 249(16):5285 (1974).
Dorland's Pocket Medical Dictionary, 24$^{th}$ edition, pp. 298–9 (1982).

* cited by examiner

Primary Examiner—Kathleen K. Fonda
Assistant Examiner—Leigh C. Maier
(74) Attorney, Agent, or Firm—Lorie Ann Morgan

(57) ABSTRACT

The present invention relates to novel amidino compound of formula (I):

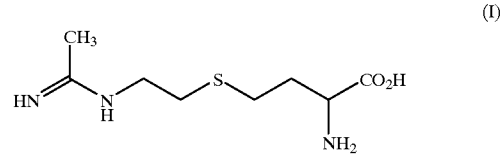

to a process for their manufacture, to pharmaceutical compositions containing them, and to their use in therapy, in particular their use as selective inhibitors of inducible nitric oxide synthase.

15 Claims, No Drawings

NITRIC OXIDE SYNTHASE INHIBITORS

This Application a continuation of U.S. patent application Ser. No. 09/341,220, filed Aug. 24, 1999, now U.S. Pat. No. 6,369,272, which application was filed pursuant to 35 U.S.C. §371 as a United States National Phase Application of International Application No. PCT/EP98/00096, filed Jan. 9, 1998, which claims priority to U.S. Provisional Patent Application Ser. No. 60/069,882, filed Jan. 13, 1997.

The present invention relates to novel amidino compounds, to a process for their manufacture, to pharmaceutical compositions containing them, and to their use in therapy, in particular their use as selective inhibitors of inducible nitric oxide synthase.

Nitric oxide is the endogenous stimulator of the soluble guanylate cyclase enzyme and is involved in a number of biological actions. Excess nitric oxide production is also thought to be involved in a number of conditions, including septic shock and many inflammatory diseases. The biochemical synthesis of nitric oxide from L-arginine is catalysed by the enzyme NO synthase. Many inhibitors of NO synthase have been described and proposed for therapeutic use.

More recently, it has been an object in this field to provide NO synthase inhibitors displaying selectivity for either inducible NO synthase (iNOS) or neuronal NO synthase (nNOS) over endothelial NO synthase (eNOS).

Thus WO093113055 describes selective NO synthase inhibitors of formula:

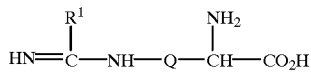

and salts, and pharmaceutically acceptable esters and amides thereof, in which:

$R_1$ is a $C_{1-6}$ straight or branched chain alkyl group, a $C_{2-6}$alkenyl group, a $C_{2-6}$alkynyl group, a $C_{3-6}$cycloalkyl group or a $C_{3-6}$cycloalkyl$C_{1-6}$alkyl group;

Q is an alkylene, alkenylene or alkynylene group having 3 to 6 carbon atoms and which may optionally be substituted by one or more $C_{1-3}$alkyl groups;

a group of formula —$(CH_2)_pX(CH_2)_q$— where p is 2 or 3, q is 1 or 2 and X is $S(O)_x$ where x is 0, 1 or 2, 0 or $NR^2$ where $R^2$ is H or $C_{1-6}$alkyl; or a group of formula —$(CH_2)_rA(CH_2)_s$— where r is 0, 1 or 2, s is 0, 1 or 2 and A is a 3 to 6 membered carbocylic or heterocyclic ring which may optionally be substituted by one or more suitable substituents such as $C_{1-6}$alkyl, $C_{1-6}$alkoxy, hydroxy, halo, nitro, cyano, trifluoro$C_{1-6}$alkyl, amino, $C_{1-6}$alkylamino or di$C_{1-6}$alkylamino.

We have now found compounds falling within the scope of WO 93/13055 which as well as being selective iNOS inhibitors, display advantages including that they have a long half-life and are orally bioavailable when administered in vivo.

Therefore, according to the present invention there is provided a compound of formula (I):

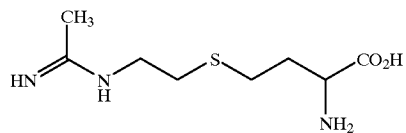

or a salt, solvate, or physiologically functional derivative thereof.

Formula (I) includes an asymmetric centre in the amino acid group, and although the natural L or (S) configuration of arginine is preferred, it is intended that formula (I) includes both (S) and (R) enantiomers either in substantially pure form or admixed in any proportions.

Thus, in the alternative, the present invention provides a compound selected from:

(R/S)-[2-(1-iminoethylamino)ethyl]-DL-homocysteine
(S)-[2-(1-iminoethylamino)ethyl]-L-homocysteine; and
(R)-[2-(1-iminoethylamino)ethyl]-D-homocysteine and salts, solvates, and physiologically functional derivatives thereof.

In a preferred aspect, the present invention provides (S)-[2-(1-iminoethylamino)ethyl]-L-homocysteine or a salt, solvate, or physiologically functional derivative thereof. In a particularly preferred aspect, the present invention provides (S)-[2-(1-iminoethylamino)ethyl]-L-homocysteine or a salt thereof.

Salts and solvates of compounds of formula (I) which are suitable for use in medicine are those wherein the counterion or associated solvent is pharmaceutically acceptable. However, salts and solvates having non-pharmaceutically acceptable counterions or associated solvents are within the scope of the present invention, for example, for use as intermediates in the preparation of other compounds of formula (I) and their pharmaceutically acceptable salts, solvates, and physiologically functional derivatives.

By the term "physiologically functional derivatives" is meant a chemical derivative of a compound of formula (I) having the same physiological function as the free compound of formula (I), for example, by being convertible in the body thereto. According to the present invention, examples of physiologically functional derivatives include esters, amides, and carbamates; preferably esters and amides.

Suitable salts according to the invention include those formed with both organic and inorganic acids or bases. Pharmaceutically acceptable acid addition salts include those formed from hydrochloric, hydrobromic, sulphuric, citric, tartaric, phosphoric, lactic, pyruvic, acetic, trifluoroacetic, succinic, oxalic, fumaric, maleic, oxaloacetic, methanesulphonic, ethanesulphonic, p-toluenesulphonic, benzenesulphonic, and isethionic acids. Pharmaceutically acceptable base salts include ammonium salts, alkali metal salts such as those of sodium and potassium, alkaline earth metal salts such as those of calcium and magnesium and salts with organic bases such as dicyclohexyl amine and N-methyl-D-glucamine.

Pharmaceutically acceptable esters and amides of the compounds of formula (I) may have the acid group converted to a $C_{1-6}$-alkyl, aryl, aryl $C_{1-6}$-alkyl, or amino acid ester or amide. Pharmaceutically accceptable amides and carbamates of the compounds of formula (I) may have an amino group converted to a $C_{1-6}$alkyl, aryl, aryl $C_{1-6}$alkyl, or amino acid amide or carbamate.

As mentioned above, the compounds of formula (I) are inhibitors of NO synthase as demonstrated in the NOS inhibition assays below.

Therefore, compounds of formula (I) and their pharmaceutically acceptable salts, solvates, and physiologically functional derivatives have use in the prophylaxis and treatment of clinical conditions for which an inhibitor of NO synthase is indicated, in particular, an inhibitor of iNOS. Such conditions include inflammatory conditions, shock states, immune disorders, and disorders of gastrointestinal motility. The compounds of formula (I) and pharmaceutically acceptable salts, solvates, and physiologically functional derivatives thereof may also be of use in the prophylaxis and treatment of diseases of the central nervous system including migraine.

By shock states is meant those resulting from overproduction of NO, such as septic shock, haemorrhagic shock, traumatic shock, or shock caused by fulminant hepatic failure or by therapy with cytokines such as TNF, IL-1 and IL-2 or therapy with cytokine-inducing agents, for example 5,6-dimethylxanthenone acetic acid.

Examples of inflammatory conditions and immune disorders include those of the joint, particularly arthritis (e.g. rheumatoid arthritis, osteoarthritis, prosthetic joint failure), or the gastrointestinal tract (e.g. ulcerative colitis, Crohn's disease, and other inflammatory bowel diseases, gastritis and mucosal inflammation resulting from infection, the enteropathy provoked by non-steroidal antiinflammatory drugs), of the lung (e.g. adult respiratory distress syndrome, asthma, cystic fibrosis, or chronic obstructive pulmonary disease), of the heart (e.g. myocarditis), of nervous tissue (e.g. multiple sclerosis), of the pancreas (e.g. diabetes melitus and complications thereof), of the kidney (e.g. glomerulonephritis), of the skin (e.g. dermatitis, psoriasis, eczema, urticaria), of the eye (e.g. glaucoma) as well as of transplanted organs (e.g. rejection) and multi-organ diseases (e.g. systemic lupus erythematosis) and inflammatory sequelae of viral or bacterial infections.

Furthermore, there is evidence for overproduction of NO by iNOS in atherosclerosis and following hypoxic or ischaemic insults (with or without reperfusion), for example in the brain or in ischaemic heart disease.

Disorders of gastrointestinal motility include ileus, for example post-operative ileus and ileus during sepsis.

By diseases of the central nervous system is meant those for which overproduction of NO is implicated, for example migraine, psychosis, anxiety, schizophrenia, sleep disorders, cerebral ischaemia, CNS trauma, epilepsy, multiple sclerosis, AIDS dementia, chronic neurodegenerative disease (e.g. Lewy Body Dementia, Huntington's disease, Parkinson's disease, or Alzheimer's disease) and acute and chronic pain, and conditions in which non-adrenergic non-cholinergic nerve may be implicated such as priapism, obesity and hyperphagia.

Examples of acute pain include musculoskeletal pain, post operative pain and surgical pain. Examples of chronic pain include chronic inflammatory pain (e.g. rheumatoid arthritis and osteoarthritis), neuropathic pain (e.g. post herpetic neuralgia, diabetic neuropathies associated with diabeties, trigeminal neuralgia, pain associated with functional bowel disorders, e.g. irritable bowel syndrome, non cardiac chest pain and sympathetically maintained pain) and pain associated with cancer and fibromyalgia.

Furthermore, inhibition of NO synthase may be of advantage in preventing the lymphocyte loss associated with HIV infection, in increasing the radiosensitivity of tumours during radiotherapy and in reducing tumour growth, tumour progression, angiogenesis, and metastasis.

Accordingly, the present invention provides a method for the prophylaxis or treatment of a clinical condition in a mammal, such as a human, for which an inhibitor of nitric oxide synthase, for example, an iNOS inhibitor is indicated, which comprises administration of a therapeutically effective amount of a compound of formula (I), or a pharmaceutically acceptable salt, solvate, or physiologically functional derivative thereof. In particular, the present invention provides a method for the prophylaxis or treatment of an inflammatory and/or immune disorder, such as arthritis or asthma. In a preferred aspect the present invention provides a method for the prophylaxis or treatment of a clinical condition selected from arthritis, asthma, ileus, and migraine.

In the alternative, there is also provided a compound of formula (I) or a pharmaceutically acceptable salt, solvate, or physiologically functional derivative thereof for use in medical therapy, particularly, for use in the prophylaxis or treatment of a clinical condition in a mammal, such as a human, for which an inhibitor of nitric oxide synthase, for example an iNOS inhibitor, is indicated. In particular, there is provided a compound of formula (I) or a pharmaceutically acceptable salt, solvate, or physiologically functional derivative thereof for the prophylaxis or treatment of an inflammatory and/or immune disorder, such as arthritis or asthma. In a preferred aspect, there is provided a compound of formula (I) or a pharmaceutically acceptable salt, solvate, or physiologically functional derivative thereof for the prophylaxis or treatment of arthritis, asthma, ileus, and migraine.

The amount of a compound of formula (I), or a pharmaceutically acceptable salt, solvate or physiologically functional derivative thereof which is required to achieve a therapeutic effect will, of course, vary with the particular compound, the route of administration, the subject under treatment, and the particular disorder or disease being treated. The compounds of the invention may be administered orally or via injection at a dose of from 0.1 to 1500 mg/kg per day, preferably 0.1 to 500 mg/kg per day. The dose range for adult humans is generally from 5 mg to 35 g/day and preferably 5 mg to 2 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg.

While it is possible for the compound of formula (I), or a pharmaceutically acceptable salt, solvate, or physiologically functional derivative thereof to be administered alone, it is preferable to present it as a pharmaceutical formulation.

Accordingly, the present invention further provides a pharmaceutical formulation comprising a compound of formula (I) or a pharmaceutically acceptable salt, solvate, or physiologically functional derivative thereof, and a pharmaceutically acceptable carrier or excipient, and optionally one or more other therapeutic ingredients.

The present invention also provides the use of a compound of formula (1), or a pharmaceutically acceptable salt, solvate, or physiologically functional derivative thereof in the manufacture of a medicament for the prophylaxis or treatment of a clinical condition for which an inhibitor of nitric oxide synthase, for example an iNOS inhibitor, is indicated, for example an inflammatory and/or immune disorder, such as arthritis or asthma. In a preferred aspect, there is provided a compound of formula (I), or a pharmaceutically acceptable salt, solvate, or physiologically functional derivative thereof in the manufacture of a medicament for the prophylaxis or treatment of a clinical condition selected from arthritis, asthma, ileus, and migraine.

Hereinafter, the term "active ingredient" means a compound of formula (I), or a pharmaceutically acceptable salt, solvate, or physiologically functional derivative thereof.

The formulations include those suitable for oral, parenteral (including subcutaneous, intradermal, intramuscular, intravenous and intraarticular), inhalation (including fine particle dusts or mists which may be generated by means of various types of metered dose pressurised aerosols, nebulisers or insufflators), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose an acacia.

Preferred unit dosage formulations are those containing an effective dose, as hereinbefore recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

According to a further aspect of the invention, there is provided a process for preparing a compound of formula (I) or a salt, solvate, or physiologically functional derivative thereof which comprises:

(i) reaction of the compound of formula (II)

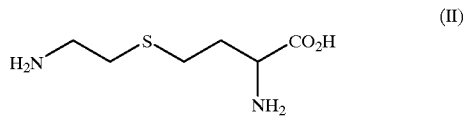

(II)

or an enantiomer, a salt, or a protected derivative thereof, with a compound of formula (III)

(III)

or a salt thereof, wherein L is a leaving group, most suitably a $C_{1-6}$ alkoxy group, for example ethoxy, or an alkylthio, aralkylthio or arylthio group e.g. a benzylthio, or 1- or 2-naphthylmethylthio group; followed by the following steps in any order:

(ii) optional removal of any protecting groups;

(iii) optional separation of an enantiomer from a mixture of enantiomers;

(iv) optional conversion of the product to a corresponding salt, solvate, or physiologically functional derivative thereof.

When L is $C_{1-6}$ alkoxy, the reaction in step (i) above may be effected in solution at alkaline pH, for example pH 8 to 11, suitably at pH 10.5, and at a low temperature, for example −5° C. to 20° C., suitably 0 to 5° C. When L is an alkylthio, aralkylthio, or arylthio group, the reaction may be effected in an organic solvent e.g. tetrahydrofuran or a $C_{1-4}$ alcohol such as ethanol, at a moderate temperature e.g. 10 to 40° C., suitably at ambient temperature.

Compounds of formula (III) and salts thereof are available commercially or may be prepared by methods of organic chemistry well known to the person skilled in the art, for example, as described by Shearer et al in Tetrahedron Letters, 1997, 38, 179–182.

Compounds of formula (II) and salts and protected derivatives thereof may be prepared from homocystine:

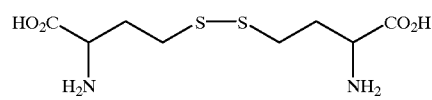

or a protected derivative thereof, by cleaving the disulphide bond to form homocysteine or a protected derivative thereof, and coupling with a compound of formula (IV):

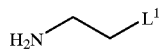

(IV)

or a protected derivative thereof, wherein $L^1$ is a leaving group, for example halo, such as bromo, or an alkyl, aryl or aralkyl sulphonate ester, such as toluenesulphonyl.

Cleavage of the disulphide linkage of homocystine or a protected derivative thereof to form homocysteine or a protected derivative thereof may be effected by methods known to the person skilled in the art, for example, by use of sodium in liquid ammonia, dithiothreitol, or sodium borohydride.

Protected derivatives of homocysteine, eg N-t-butoxycarbonyl homocysteine t-butyl ester, may react with compounds of formula (IV) under conditions in an appropriate organic solvent (eg toluene) in a reaction mediated by a base such as 1,8-diazabicyclo[5.4.0]undec-7-ene or a similar agent which would be recognised by one skilled in the art.

Homocystine, the compounds of formula (IV) and protected derivatives thereof are commercially available or may be prepared by methods of organic chemistry well known to the person skilled in the art.

The protecting groups used in the preparation of compounds of formula (I) may be used in a conventional manner, for example, using methods described in "Protective Groups in Organic Synthesis" by Theodora W Green, 2nd edition (John Wiley and Sons, 1991) which also describes methods for the removal of such groups.

In the above reactions, primary amines are suitably protected using acyl groups, such as t-butoxycarbonyl or benzyloxycarbonyl groups which may be removed under acidic conditions, for example, by treatment with hydrochloric acid or hydrobromic acid, or by hydrogenolysis.

As will be appreciated by the person skilled in the art use of such protecting groups may include orthogonal protection of amino groups in the compounds of formula (II) to facilitate the selective removal of one group in the presence of another, thus enabling selective functionalisation of a single amino function. For example, a benzyloxycarbonyl group may be selectively removed by hydrogenolysis. A person skilled in the art will also appreciate other orthogonal protection strategies, available by conventional means as described in Theodora W Green (vide supra).

The enantiomeric compounds of the invention may be obtained (a) by separation of the components of the corresponding racemic mixture, for example, by means of a chiral chromatography column, enzymic resolution methods or preparing and separating suitable diastereoisomers, or (b) by direct synthesis from the appropriate chiral intermediates by the methods described above.

Optional conversion of a compound of formula (I) to a corresponding salt may conveniently be effected by reaction with the appropriate acid or base. Optional conversion of a compound of formula (I) to a corresponding solvate or physiologically functional derivative may be effected by methods known to those skilled in the art.

According to a further aspect, the present invention provides novel intermediates for the preparation of compounds of formula (I), for example: compounds of formula (II) as defined above, or an enantiomer, a salt, or a protected derivative thereof, particularly, a compound selected from:

(S)-2,7-diamino-5-thioheptanoic acid;
(S)-7N-benzyloxycarbonyl-2,7-diamino-5-thioheptanoic acid;
(R,S)-2,7-diamino-5-thioheptanoic acid;
(R,S)-7N-benzyloxycarbonyl-2,7-diamino-5-thioheptanoic acid;
(S)-2N-t-butoxycarbonyl-2,7-diamino-5-thioheptanoic acid;
(S)-2N-t-butoxycarbonyl-7N-benzyloxycarbonyl-2,7-diamino-5-thioheptanoic acid;
(S)-t-butyl-2N-t-butoxycarbonyl-7N-benzyloxycarbonyl-2,7-diamino-5-thioheptanoate;
(S)-t-butyl-2N-t-butoxycarbonyl-2,7-diamino-5-thioheptanoate;
(R,S)-2N-t-butoxycarbonyl-2,7-diamino-5-thioheptanoic acid;
(R,S)-2N-t-butoxycarbonyl-7N-benzyloxycarbonyl-2,7-diamino-5-thioheptanoic acid;
(R,S)-t-butyl-2N-t-butoxycarbonyl-7N-benzyloxycarbonyl-2,7-diamino-5-thioheptanoate; and
(R,S)-t-butyl-2N-t-butoxycarbonyl-2,7-diamino-5-thioheptanoate.

Certain protected derivatives of the compounds of formula (I) are also useful as intermediates for the preparation of compounds of formula (I) particularly a compound selected from:

(S)-2N-t-butoxycarbonyl-7N-(1-iminoethyl)-2,7-diamino-5-thioheptanoic acid;
(S)-t-Butyl-2N-t-butoxycarbonyl-7N-(1-iminoethyl)-2,7-diamino-5-thioheptanoate;
(R,S)-2N-t-butoxycarbonyl-7N-(1-iminoethyl)-2,7-diamino-5-thioheptanoic acid;
(R,S)-t-Butyl-2N-t-butoxycarbonyl-7N-(1-iminoethyl)-2,7-diamino-5-thioheptanoate;
and salts and solvates thereof.

For a better understanding of the invention, the following Examples are given by way of illustration.

SYNTHETIC EXAMPLES

Example 1

Synthesis of (S)-f2-(1-iminoethylamino)ethyl-L-homocysteine or (S)-7N-(1-iminoethyl)-2,7-diamino-5-thioheptanoic Acid (i) (S)-7N-benzyoxcyarbonyl-2,7-diamino-5-thioheptanoic Acid To liquid ammonia (130 mL), cooled to −80° C., was added L-homocystine (3 g), followed by sodium metal (1.06 g) until the blue colour persisted for 15 min. After this time N-benzyloxycarbonyl-ethanolamine tosylate (8.16 g) was added and the reaction stirred at ambient temperature until the ammonia had evaporated. The residue was dissolved in water (80 mL) and treated with 0.5 M EDTA.sodium salt (2 mL). The pH of the solution was adjusted to 7.0 with 2N sulphuric acid and the resulting white precipitate filtered off, washed with cold water and acetone and dried in a vacuum dessicator to yield the title compound as a white solid, 5.3 g.

Mass Spectrum M+H 313

(ii) (S)-2,7-diamino-5-thioheptanoic Acid (S)-7N-benzyloxycarbonyl-2,7-diamino-5-thioheptanoic acid (5.3 g) was treated with 45% HBr in acetic acid (23 mL) for 1 h. An intractable gum was formed and either was added to the mixture to ensure complete precipitation of the product. The liquid was decanted off and the solids dissolved in hot SVM. This hot solution was treated with pyridine until a precipitate just persisted and the mixture allowed to cool to room temperature. The resulting precipitate was filtered off and recrystallised from SVM/water to yield the title compound as a white solid, 2.2 g, mp 222° C.(dec).

(iii) (S)-[2-(1-iminoethylamino)ethyl]-L-homocysteine (S)-2,7-Diamino-5-thioheptanoic acid (2.17 g) was stirred in 1N NaOH (16.75 mL) to pH 10.5 at 0–5° C. To this solution was added ethyl acetimidate hydrochloride (2.07 g) portionwise, maintaining the pH at 10.5 with 1N NaOH. When the reaction was complete the pH was adjusted to 3 with 1N HCl and the mixture applied to a Dowex AGX8 H+ form ion exchange column. The column was washed to neutral, then with 2.5M pyridine and again to neutral with water. Elution with 0.5M ammonia and collection of the ninhydrin positive fractions, gave after evaporation. The resulting residue was treated with 1N HCl to pH 4.5, evaporated to dryness. The residue was then treated with ethanol and evaporated to dryness and then with diethyl ether and diethyl ether and evaporated to dryness to give the monohydrochloride of the title compound as a hard white foam.

The microanalysis of the product was consistent with the 1.75 hydrate: found (calculated): C 33.56 (33.45); H 7.11 (7.49), N 13.74 (14.63)

Example 2

(R/S)-[2-(1-iminoethylamino)ethyl]-D,L-homocysteine was prepared by methods analogous to those used in Example 1, starting from D,L-homocystine.

The $^1$H NMR of the product was consistent with the proposed structure.

Example 2a

The racemic product of Example 2 was substantially resolved into the two constituent enantiomers [identical to the (S) product in Examples 1 and 4 and the (R) product in Example 3] using a chiral Crownpac (+) HPLC column and elution with aqueous trifluoroacetic acid at pH2.

(S)-[2-(1-iminoethylamino)ethyl]-L-homocysteine

The microanalysis of the product was consistent with the ditrifluoroacetate salt hydrate $C_8H_{17}N_3O_2S.(CF_3CO_2H)_2.H_2O$ found (calculated): C 31.06 (30.97); H 4.53 (4.55), N 9.08 (9.03) CD spectrum (0.1N aq HCl) 210 (+0.80) nm.

(R)-[12-(1-iminoethylamino)ethyl]-D-homocysteine

The microanalysis of the product was consistent with the salt form .1.67 trifluoroacetate .0.3 HCl .1.5hydrate $C_8H_{17}N_3O_2S.(CF_3CO_2H)_{1.67}HCl_{0.3}.1.5H_2O$ found (calculated): C 30.18 (30.40); H 4.92 (4.97), N 9.53 (9.41), S 7.41 (7.18), Cl 1.86 (2.38), F 21.36 (21.28).

CD Spectrum (0.1N aq HCl) 210 (−0.64) nm.

Example 3

(R)-[2-(1-iminoethylamino)ethyl]-D-homocysteine was prepared by methods analogous to those used in Example 1, starting from D-homocystine.

Example 4

Synthesis of (S)-[2-(1-iminoethylamino)ethyl]-L-homocysteine (i) (S)-7N-benzyloxycarbonyl-2,7-diamino-5-thioheptanoic Acid To liquid ammonia (430 mL) cooled to −80° C., was added L-homocystine (10 g, 37.45 mmol). The cooling bath was removed and sodium metal (3.18 g, 138.26 mmol) was added portionwise over 25 min allowing the temperature to rise to reflux temperature. Stirring was continued at reflux for a further 30 min, after which time N-benzyloxycarbonyl-ethanolamine tosylate (25 g, 74.9 mmol) was added and the reaction stirred at ambient temperature overnight until the ammonia had evaporated. The residue was stirred with water (250 mL) at 40° C. for 10 min, cooled to room temperature and filtered. The pH of the solution was adjusted to 7.0 with 2M sulphuric acid and the resulting white precipitate filtered off, washed with cold water and acetone and dried in a vacuum dessicator to yield (S)-7N-benzyloxycarbonyl-2,7-diamino-5-thioheptanoic acid as a white solid, Mp 240° C.(dec).

(ii) (S)-2N-t-butoxycarbonyl-7N-benzyloxycarbonyl-2,7-diamino-5-thioheptanoic Acid (S)-7N-benzyloxycarbonyl-2,7-diamino-5-thioheptanoic acid (15.5 g, 49.67 mmol) was added to sodium hydroxide (6.357 g, 159 mmol) in water (110 mL) followed by dioxane (55 mL). To this mixture was added di-t-butyldicarbonate (16.26 g, 74.5 mmol) and the mixture stirred overnight at room temperature under nitrogen. After this time the precipitated solids were filtered off, toluene (300 mL) added, and the layers separated. The aqueous layer was cooled and made acidic to pH ~3 using 1 N HCl. The acidified fraction was extracted with toluene (4×100 mL) and ethyl acetate (3×100 mL), and the combined organic fractions dried over MgSO$_4$. Concentration of the combined organics under reduced pressure to give (S)-2N-t-butoxycarbonyl-7N-benzyloxycarbonyl-2,7-diamino-5-thioheptanoic acid as a white gum. Mmass spectrum M+H 413

(iii) (S)-2N-t-butoxycarbonyl-2.7-diamino-5-thioheptanoic Acid Formate Salt

To methanol (50 mL) cooled to 5° C. under a nitrogen atmosphere was added palladium black (0.678 g) all at once. To this cooled solution was added a mixture of methanol (50 mL) and formic acid (11 mL, 196 mmol) over 1 min followed by the addition of (S)-2N-t-butoxycarbonyl-7N-benzyloxycarbonyl-2,7-diamino-5-thioheptanoic acid (2 g, 4.85 mmol) in methanol (50 mL) over 2 min. The mixture was allowed to stir overnight at ambient temperature, more palladium black (257 mg) added and stirring continued for a further 3 h. The reaction mixture was filtered through Hyflo and concentrated under reduced pressure. The residue was partitioned between water and ethyl acetate, the aqueous layer washed with more ethyl acetate, and the aqueous layer concentrated to yield (S)-2N-t-butoxycarbonyl-2,7-diamino-5-thioheptanoic acid formate salt as a white solid.

Mass Spectrum M+H 279 (65%), 223 (100%)

(iv) (S)-2N-t-butoxycarbonyl-7N-(1-iminoethyl)-2,7-diamino-5-thioheptanoic Acid Hydrochloride To (S)-2N-t-butoxycarbonyl-2,7-diamino-5-thioheptanoic acid formate salt (2.154 g, 6.59 mmol) in ethanol (50 mL) at room temperature under nitrogen was added S-(1-naphthylmethyl)thioacetimidate hydrochloride (3.70 g, 14.75 mmol) followed by ethanol (50 mL). Stirring at ambient temperature, the solids dissolved after 2 h and the solution stirred overnight. The reaction was concentrated in vacuo, the residue treated with water, and the aqueous fraction washed with diethyl ether (4×50 mL). Concentration of the aqueous fraction in vacuo gave (S)-2N-t-butoxycarbonyl-7N-(1-iminoethyl)-2,7-diamino-5-thioheptanoic acid hydrochloride as a white hygroscopic solid.

Mass spectrum M+H 320 (75%), 264 (100%), 220 (15%)

(v) (S)-[2-(1-iminoethylamino)ethyl]-L-homocysteine

To (S)-2N-t-butoxycarbonyl-7N-(1-iminoethyl)-2,7-diamino-5-thioheptanoic acid hydrochloride (3.086 g, 8.69 mmol) was added slowly 4N HCl/dioxane (20 mL) and the reaction mixture stirred at ambient temperature overnight. The reaction was concentrated in vacuo, the residue dissolved in water and washed with diethyl ether (3×20 mL).

The aqueous layer was concentrated in vacuo to yield the title compound as the hydrochloride, as a hygroscopic solid.

Mass Spectrum M+H 220;

$^1$H NMR(D$_2$O) δ: 2.1–2.35 (5H,m), 2.76 (2H,t), 2.87 (2H,t), 3.51 (2H,t), 4.12 (1H,t).

Example 5

Synthesis of (S)-[2-(1-iminoethylamino)ethyl]-L-homocysteine (i) (S)-t-butyl-2N-t-butoxycarbonyl-7N-benzyloxycarbonyl-2,7-diamino-5-thioheptanoate To a solution of N-t-butoxycarbonyl cysteine t-butyl ester (prepared by reduction of N-t-butoxycarbonyl cystine t-butyl ester with dithiothreitol) (291 mg, 1 mmol) in dry toluene (20 ml) is added N-benzyloxycarbonyl ethanolamine tosylate (349 mg, 1 mmol) and 1,8diazabicyclo[5.4.0]undec-7-ene (150 μL, 1 mmol) and the mixture stirred vigorously overnight at room temperature under nitrogen. The mixture is partitioned between 50 ml each of ethyl acetate and 1N aqueous HCl. A further organic extract is combined and these extracts washed with aqueous sodium bicarbonate, water and brine, then dried and evaporated. Purification by column chromatography affords the title compound.

Mass Spectrum M+H 469 (25%), 369 (100%)

In an alternative method, conversion of the product from Example 4, step (ii) to its t-butyl ester using either N,N-dimethylformamide di-O-t-butyl acetal or O-t-butyl 1,1,1 trichloroacetimidate gave the title compound as a white crystalline solid.

(ii) (S)-t-butyl-2N-t-butoxycarbonyl-2.7-diamino-5-thioheptanoate Formate Salt

To a solution of (S)-t-butyl-2N-t-butoxycarbonyl-7N-benzyloxycarbonyl-2,7-diamino-5-thioheptanoate (1 g, 2.1 mmol) in ethanol (50 ml) was added palladium hydroxide on carbon (20%, 0.5 g) and ammonium formate (1.34 g). The suspension was refluxed for 2.5 h, cooled and filtered through a plug of silica which was well washed with 1:1ethanol-water and evaporated to afford the title compound as a formate salt.

Mass Spectrum M+H 335

(iii) (S)-t-Butyl-2N-t-butoxycarbonyl-7N-(1-iminoethyl)-2,7-diamino-5-thioheptanoate Hydrochloride The crude (S)-t-butyl-2N-t-butoxycarbonyl-2,7-diamino-5-thioheptanoate formate salt from step (ii) was slurried with 50 ml of tetrahydrofuran, the liquid decanted and mixed with S-(1-naphthylmethyl)thioacetimidate hydrochloride (0.5 g, 2 mmol) and stirred for 24 hours at room temperature. The solvent was evaporated and the residue partitioned between 25 ml each of ether and water, followed by 2 ether washes; back aqueous extracts were combined and evaporated to give a white paste. This was freeze dried twice to afford the title compound as a white hygroscopic solid.

Mass spectrum M+H 376 (100%), 320 (15%), 276 (12%).

(iv) (S)-S-[2-(1-iminoethylamino)ethyl]-L-homocysteine

Deprotection of (S)-t-Butyl-2N-t-butoxycarbonyl-7N-(1-iminoethyl)-2,7-diamino-5-thioheptanoate hydrochloride using 4N HCl in dioxane, by methods analogous to those used in Example 4 step (v), afforded (S)-S-[2-(1-iminoethylamino)ethyl]-L-homocysteine.

The characterising data for the title compound was consistent with that for the product of Example 4.

Biological Activity

1. Inhibition of eNOS and iNOS in Rat Aortic Rings

The inhibition of eNOS and iNOS in situ in rat aortic rings was assessed by measuring the increases in ring tension caused by NO synthase inhibition. For studies of basal tone (reflecting eNOS), rings of thoracic aorta with intact endothelium were prepared as described previously (Rees et al. (1989) Br. J. Pharmol. 96, 418–424) and cumulative concentration curves obtained for the inhibitors in the presence of a threshold concentration of phenylephrine (ED$_{10}$≈10 nM). For studies of induced smooth muscle tone (reflecting iNOS), endothelium-denuded rings were exposed to LPS (0.1 μ/ml from S. typhosa) in the presence of phenylephrine at approximately ED$_{90}$ for 6 h as described previously (Rees et al. (1990) Biochem. Biophys. Res. Commun. 173, 541–547). During this time a progressive loss of tone occurred because of iNOS induction. Cumulative concentration curves were then obtained for the inhibitors.

The results are given in the following table:

|  | iNOS IC$_{50}$(μM) | eNOS % inhib @ 300 μM | selectivity iNOS vs eNOS |
|---|---|---|---|
| Example 1 | 0.73 | 43 | >500 fold |
| Example 2 | 0.45 | 53 | >500 fold |
| Example 3 | 6.6 | 20 | >150 fold |

By contrast, 2-(1-iminoethylamino)ethyl cysteine hydrochloride (Example 4 of W093/13055) is only 33 fold selective for iNOS versus eNOS in the same test.

2. Inhibition of nNOS in Rat Cortical Slices

The effects of compounds on nNOS in rat brain slices was determined as described in Furfine et al (1994) J. Biol. Chem. 269. 26677–26683 and Lizasoain et al (1995) J. Neurochem. 64, 636–642.

KCl (54 mM)—stimulated NO synthesis was measured by the conversion of 14C-arginine to 14C-citrulline over a 2 h period at 37° C. in McIlwain—chopped (0.2 mm×0.2 mm) rat cerebral cortex slices, following a 1 h preincubation period in the absence of compound or high KCl.

The compound of Example 1 was determined to have an IC$_{50}$ of 220 μM, suggesting approximately 300-fold selectivity for iNOS versus nNOS.

3. Method for Determining the Oral Bioavailability of iNOS Inhibitor Compounds

Animal Work:

Mice (3 animals per time point) were dosed intravenously (10 mg/kg) and orally (50 mg/kg) with test compound in an aqueous solution. Blood samples were taken at time intervals after administration and plasma prepared by centrifugation. Samples were stored at −20° C. until analysis.

Analysis of Compounds in Plasma

Plasma (50 μl) was de-proteinated and compound derivatised with a quaternary ammonium reagent. Samples were then injected onto an HPLC system and compound concentration determined using mass spectrometric detection.

Pharmacokinetic Analysis

The plasma concentrations obtained by the above method were entered into a pharmacokinetic software package (PKCAL v 1.2 s) and the data were fitted using a non-compartmental method. The oral bioavailability of the compounds was determined by comparing the Area Under the Curve (AUC) values calculated by the software for the oral profile with the AUC for the intravenous profile The half-lives were obtained by fitting the terminal phase time points of the intravenous profile.

(S)-[2-(1-iminoethylamino)ethyl]-L-homocysteine was found to have an oral bioavailability of 55% and a half-life of 5.7 h.

When repeated at iv and oral doses of 10 mg/kg in rats, (S)-[2-(1-iminoethylamino)ethyl]-L-homocysteine had a bioavailability of 92%.

What is claimed is:

1. A method for the prophylaxis or treatment of neuropathic pain in a mammal, said method comprising administering to said mammal a therapeutically effective amount of a compound of formula (I):

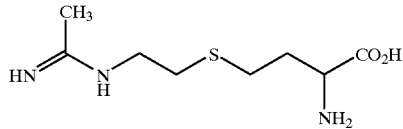

(I)

or a salt, solvate, or physiologically functional derivative thereof.

2. The method according to claim 1, wherein said mammal is a human.

3. The method according to claim 1, wherein said compound of formula (I) is (S)-[2-(1-iminoethylamino)ethyl]-L-homocysteine or a salt, solvate or physiologically functional derivative thereof.

4. A method for the prophylaxis or treatment of irritable bowel syndrome in a mammal, said method comprising administering to said mammal a therapeutically effective amount of a compound of formula (I):

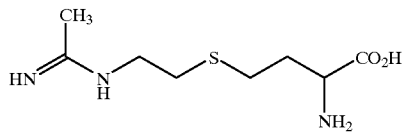

(I)

or a salt, solvate, or physiologically functional derivative thereof.

5. The method according to claim 4, wherein said mammal is a human.

6. The method according to claim 4, wherein said compound of formula (I) is (S)-[2-(1-iminoethylamino)ethyl]-L-homocysteine or a salt solvate or physiologically functional derivative thereof.

7. A method for the prophylaxis or treatment of chronic obstructive pulmonary disease in a mammal, said method comprising administering a therapeutically effective amount of a compound of formula (I):

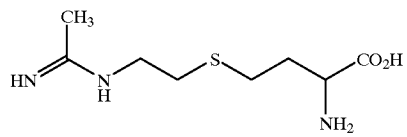

(I)

or a salt solvate, or physiologically functional derivative thereof.

8. The method according to claim 7, wherein said mammal is a human.

9. The method according to claim 7, wherein said compound of formula (I) is (S)-[2-(1-iminoethylamino)ethyl]-L-homocysteine or a salt, solvate, or physiologically functional derivative thereof.

10. A compound selected from:
   (R,S)-7N-benzyloxycarbonyl-2,7-diamino-5-thioheptanoic acid;
   (S)-t-butyl-2N-t-butoxycarbonyl-7N-benzyloxycarbonyl-2,7-diamino-5-thioheptanoate;
   (S)-t-butyl-2N-t-butoxycarbonyl-2,7-diamino-5-thioheptanoate;
   (R,S)-t-butyl-2N-t-butoxycarbonyl-7N-benzyloxycarbonyl-2,7-diamino-5-thioheptanoate; and
   (R,S)-t-butyl-2N-t-butoxycarbonyl-2,7-diamino-5-thioheptanoate.

11. (R,S)-7N-benzyloxycarbonyl-2,7-diamino-5-thioheptanoic acid or a salt thereof.

12. (S)-t-butyl-2N-t-butoxycarbonyl-7N-benzyloxycarbonyl-2,7-diamino-5-thioheptanoate or a salt thereof.

13. (S)-t-butyl-2N-t-butoxycarbonyl-2,7-diamino-5-thioheptanoate or a salt thereof.

14. (R,S)-t-butyl-2N-t-butoxycarbonyl-7N-benzyloxycarbonyl-2,7-diamino-5-thioheptanoate or a salt thereof.

15. (R,S)-t-butyl-2N-t-butoxycarbonyl-2,7-diamino-5-thioheptanoate or a salt thereof.

* * * * *